United States Patent [19]

Sager et al.

[11] Patent Number: 4,891,846
[45] Date of Patent: Jan. 9, 1990

[54] MEDICAL ABSORPTION GARMENT

[76] Inventors: Annette M. Sager, 17424 Fulton Rd., Marshallville, Ohio 44645; Suzette M. Szittai, 185 Marion St., Doylestown, Ohio 44230

[21] Appl. No.: 285,764
[22] Filed: Dec. 16, 1988
[51] Int. Cl.⁴ .......................... A41D 1/04; A41B 13/10
[52] U.S. Cl. .............................................. 2/49 R; 2/2; 2/102; 128/874; 128/888
[58] Field of Search .......................... 2/2, 2.5, 48, 49 R, 2/49 A, 50, 51, 52, 102, 103, 114, DIG. 7; 128/873, 874, 875, 888, 889, 157

[56] References Cited

U.S. PATENT DOCUMENTS

| | | | |
|---|---|---|---|
| 2,490,477 | 12/1949 | Runck | 2/52 |
| 2,675,557 | 4/1954 | Kempner, Jr. | 2/114 |
| 3,276,430 | 10/1966 | Murcott | 128/874 |
| 3,611,455 | 10/1971 | Gottfried | 128/889 |
| 4,183,097 | 1/1980 | Mellian | 2/2.5 |
| 4,608,717 | 9/1986 | Dunbavand | 2/2.5 |
| 4,648,136 | 3/1987 | Higuchi | 2/2.5 |
| 4,697,285 | 10/1987 | Sylvester | 2/2.5 |

Primary Examiner—Werner Schroeder
Assistant Examiner—Jeanette E. Chapman
Attorney, Agent, or Firm—Oldham & Oldham

[57] ABSTRACT

A medical absorption garment for use by wearers with medical appliances connected to their body in the vicinity of their upper chest or neck. The garment comprises a frontal bib member which has a neck yoke at its upper end, and an attenuated yoke panel immediately below and adjacent to the yoke's lower edge. The bib is fabricated in a laminate structure comprising at least one absorbant inner layer, with covering layers on the outside thereof. Strapping attached to the bib allows it to be temporarily fastened to the wearer.

5 Claims, 2 Drawing Sheets

MEDICAL ABSORPTION GARMENT

FIELD OF THE INVENTION

This invention relates to protective garments. More particularly, this invention relates to medical garments useful for protecting a wearer from skin contact with fluids associated with the wearer's disability and treatment. Specifically, this invention relates to bib-like vests, designed to cover the front of a wearer's upper torso, that can be worn without interfering with medical appliances connected to the wearer. Such vests have the ability to absorb moisture and liquids associated with the appliances, the treatment, and the wearer's infirmity, which are present in and around the area adjacent to the point of connection of the appliances with the wearer's skin.

A considerable number of individuals in society today suffer from physical disabilities which require that they be connected to intrusive medical appliances such as trachea tubes, Hickman-Broviac catheters, and the like. Trachea tubes, for example, are sometimes required to supply air to individuals in instances where obstructions or other problems related to the upper airways are encountered, while catheterization of a subclavian blood vessel is frequently resorted to where nourishment or medicine must be supplied intravenously to a patient. In such cases, the skin at the point of insertion of the appliance, and the surrounding area is oftentimes unavoidably subjected to exposure to body fluids and to the liquids required by the treatment.

Unfortunately, continued skin contact with such moisture not only tends to make the patient feel cold and uncomfortable, but frequently promotes the growth of yeasts or undesirable bacterial which not uncommonly lead to rashes on skin so exposed, or to infection, the point of intrusion being particularly vulnerable in this respect.

BACKGROUND OF THE INVENTION

In the past, attempts have been made to counter the problem by preventing the moisture from reaching the skin, for example, through the imposition of a moisture barrier such as plastic-backed fabric between the skin of the patient and the source of the moisture. Inevitably, however, some of the moisture eventually penetrates below the barrier, to the area of the skin, at which point it ecacerbates the problem, since it traps the moisture against the skin, preventing drying. The moisture problem is especially acute, in instances where prolonged use of a trachea tube requires the application of an aqueous mist to the outer tube opening to prevent desiccation of the patient's airways.

Aggravating the problem is the fact that when the dressings employed in association with such treatments become too wet, they must be replaced. Continual replacement of dressings not only adds to the patient's discomfort, but significantly increases the chances of unwanted infection.

DISCLOSURE OF THE INVENTION

In view of the foregoing, therefore, it is a first aspect of this invention to provide a medical absorption garment which helps to keep the wearer warm and dry, even when exposed to a damp or wet environment.

A second aspect of this invention is to provide a medical absorption garment which helps to protect the wearer from conditions which increase the risk of infection, and from other harmful or uncomfortable physical conditions.

Another aspect of this invention is the provision of a bib-like vest which is able to absorb body fluids and liquids associated with a wearer's treatment, thereby preventing their contact with the wearer's skin.

A further aspect of this invention is to furnish an absorption vest which may be worn by infants, as well as by older individuals, and which is easy to put on wearers, even when they are unable to assist in the garbing process.

An additional aspect of this invention is to provide a medical absorption vest that may be worn without interfering with a connected medical appliance, such as a trachea tube, or a subclavian catheter.

Another aspect of this invention is to provide a medical absorption garment that may either be disposed of after becoming saturated with liquid, or which may be cleaned and reused repeatedly, and which may be worn either on the inside, or outside of a wearer's clothing.

The foregoing and other aspects of this invention are provided by a medical absorption garment comprising:

a bib member;

a torso strap, and upper strapping, wherein said bib member is a laminate comprising at least one absorbant, fiberous inner layer disposed between two outer layers of fabric, said bib member being provided on its upper end with a neck yoke having an attenuated yoke panel adjacent to the lower edge thereof, and wherein said torso strap extends from one side of said bib, being adapted to and circle the torso of the wearer and to be temporarily attached to said bib member, and wherein further, said upper strapping extends from the upper end of said bib member at the side of said neck yoke, being adapted to be temporarily attached so as to secure the upper end of said bib adjacent to the neck of the wearer.

The foregoing and other aspects of the invention are also obtained by a medical absorption garment comprising:

a bib member;

a torso strap;

two shoulder straps, and strap fastening means, wherein said bib member is a laminate comprising multiple sheets of absorbant batting disposed between two outer layers of fabric, said bib member being provided on its upper end with a neck yoke having a panel adjacent the lower edge thereof attentuated by stitching, and wherein said torso strap extends from one side of said bib, being adapted to and circle the torso of a wearer and to be temporarily attached to said bib member by a strap fastening means, and wherein further said shoulder straps extend from the upper end of said bib member, one from each side of said neck yoke, being adapted to be temporarily attached to said torso strap at the rear of the wearer by strap fastening means, following extension over the shoulders of the wearer, and wherein still further, said strap fastening means comprise cooperating strips of filamentary hooks and loops, respectively, disposed as strips attached to the surface to be temporarily fastened to each other.

BRIEF DESCRIPTION OF THE DRAWINGS

The invention will be better understood when reference is had to the following drawings, in which like numbers refer to like parts and wherein.

DETAILED DESCRIPTION OF THE INVENTION

Figure 1:
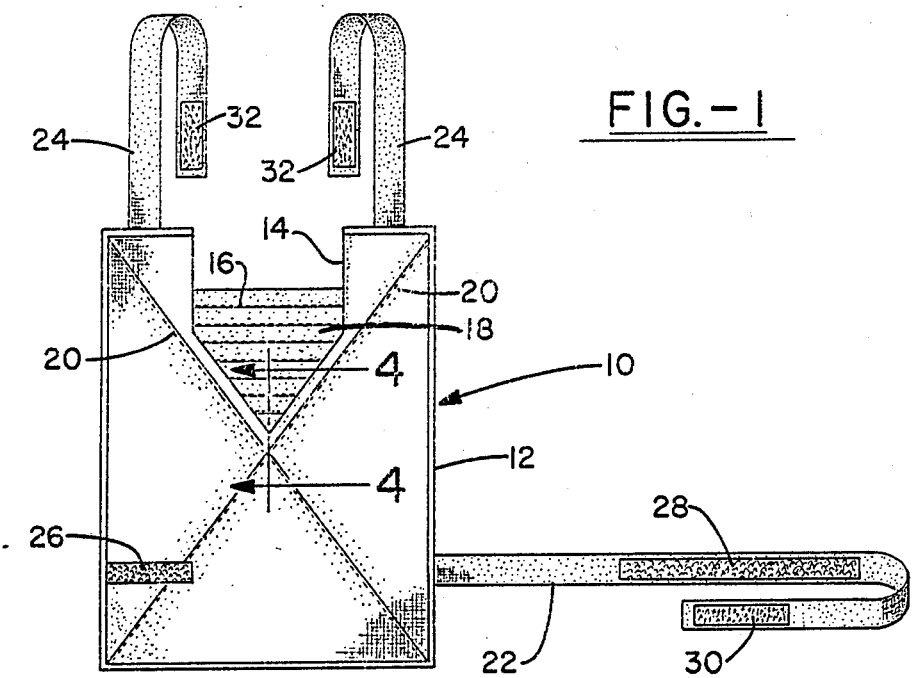
FIG. 1 is a front view of a medical absorption garment of the invention.

FIG. 1 is a front view of the medical absorption garment of the invention, generally 10.

The Figure shows a dickey or bib-like member 12 with a neck yoke 14 cut therefrom. Adjacent to the lower edge of the neck yoke 14 is a panel 18 which comprises a thinner, or attenuated portion of the bib, in the case of the garment represented in FIG. 1, such attenuation being accomplished by rows of stitching 16 which serve to compress the bib's thickness in the area of the stitching. The bib member 12 shown also includes "tack" stitching 20 to prevent the components of the laminate structure, described hereinafter, from shifting. Extending from one side of the bib member 12 is a torso strap 22, which as shown, includes strap fastening means comprising a torso strap anchor panel 28 of filamentary loops, and a torso strap attachment strip 30 of filamentary hooks. Loops and hooks of the type referred to are commonly known as "Velcro" strips, and are used where temporary attachments of components, each of which has one of such structures connected thereto, are to be made. A bib anchor panel 26 comprising filamentary loops intended to cooperatively attach the torso strap attachment strip 30, is also located on bib 12. Shoulder straps 24 extend from the upper end of the bib member 12, at the side of the neck yoke 14, the straps being provided with shoulder strap attachment strips 32, in the case of the Figure, being filamentary hooks. It should be understood that hook structures may be substituted for loop structures, or vice versa, it merely being necessary that one of each type of structure be present at a point where a connection between components is to be achieved.

The bib shown in FIG. 1 has a generally rectangular shape; however, other shapes may also be used as, for example, square, partially circular or elliptical, etc. Likewise, different shapes of the cut-out yoke may also be employed, including a semicircular yoke, one with a "Vee" shape, or others. The use of a rectangular or square shaped cut-out is preferred however, particularly with trachea tubes, since such a shape provides minimal interference with the presence of the medical appliance inserted in the patient. Yoke panel 18 may also be designed in shapes other than that of FIG. 1; for instance, it could be rectangular, square, semicircular, semi-elliptical, etc.

Although Velcro-type fastening means are illustrated, and are greatly preferred because of the case with which attachments may be made, different methods of fastening, for instance, snaps, "ties", or others might also be used if desired.

Figure 2:
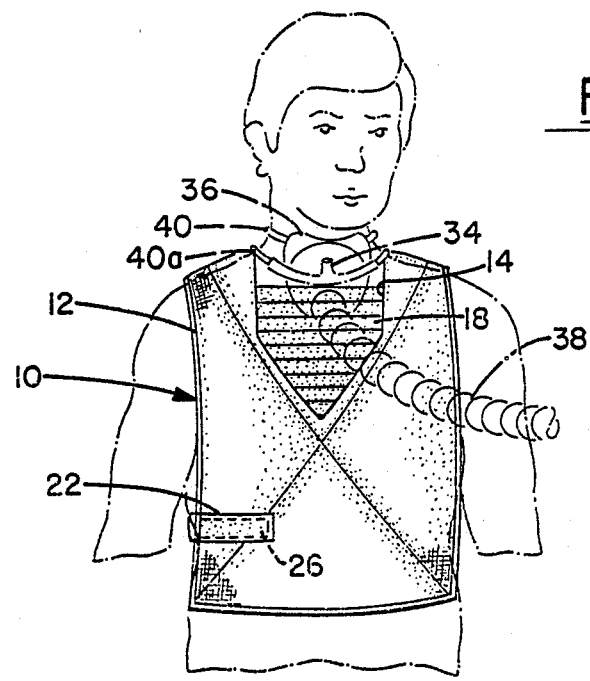
FIG. 2 is a front view of an individual wearing the garment of the invention.

FIG. 2 illustrates a front view of an individual wearing a protective garment of the invention. As shown in the Figure, the individual has been provided with a trachea tube 34, which has been inserted in the individual's trachea, or windpipe, and the tube has been enclosed by a humidifier manifold 36, the latter being connected to a manifold supply tube 38 attached to a misting device, not shown. The tracheal treatment shown is one which unavoidably entails the accumulation of considerable amounts of fluids about the upper chest and neck regions of the individual, the elimination of which is a primary purpose of the bib member 12. As shown, the yoke cut-out 14 is positioned about the neck of the wearer, with a portion of the tracheal appliance being supported on the attenuated yoke panel 18, additional support for the appliances being supplied by neck straps 40 and 40a. The bib member 12 is fastened to the individual by shoulder straps, better seen in FIG. 3, and by torso strap 22, which is permanently attached to one side of the bib 12, and which encircles the torso of the wearer, being temporarily attached to bib anchor panel 26 by the means previously described.

In order to avoid interference of the bib member 12 with the attached medical appliances, the bib is provided with a yoke panel 18 which is thinner than the rest of the bib. The panel may be attached as a separate, thinner member, however it has been found considerably preferable to simply form the panel by compressing or "attenuating" a section of the bib member 12. Such attenuation is conveniently achieved by supplying the yoke panel 18 with closely spaced stitching. Such stitching may take the form of closely spaced parallel rows of stitching, or the stitching may be provided in other patterns, or it may be random. The "quilting" structure thus achieved, has the advantage of retaining its absorbency, while at the same time being sufficiently thinner than the balance of the bib 12 to avoid interference with the associated medical appliance. Furthermore, the quilting seems to have an "anchoring" effect on the structure of the medical appliance, preventing it from slipping, and providing desirable support therefore. The dimensions of the panel are relatively unimportant, and will depend upon the nature of the appliance involved; however, it is of course desirable that the panel have an area adequate to at least be co-extensive with the area of the appliance with which it is in contact.

While the bib is admirably suited for use with infants and small children, its size may be altered as required to be equally useful with older individuals, including adults. Appropriate fits can be obtained simply by altering the dimensions of the bib portion and the strapping to accommodate the wearer's body size.

Figure 3:
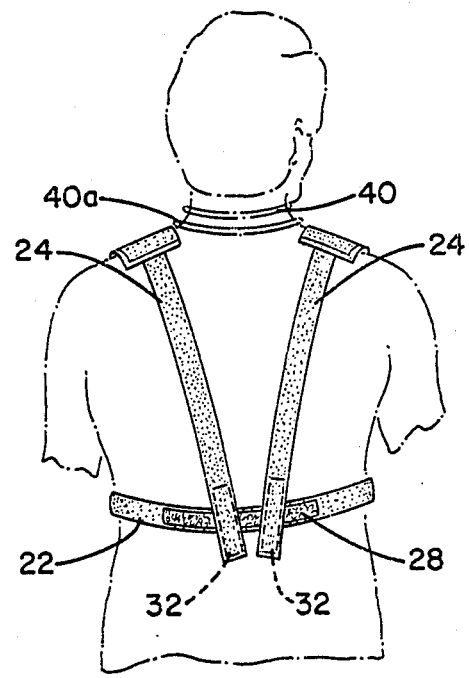
FIG. 3 is a rear view of an individual wearing the medical absorption garment of the invention.

FIG. 3 is a rear view of an individual provided with a medical appliance, and wearing the garment of the invention. In the Figure, portions of the appliance, including the manifold supply tube 38, and neck straps 40 and 40a are shown, as are the shoulder straps 24, attached to the torso strap 22 by means of the torso strap anchor panel 28. While other forms of strapping might be used, for example, strapping encircling the back of the neck extending from the side of the neck yoke, the use of two shoulder straps, as shown, has significant advantages, and is therefore preferred. It can be disposed in a criss-cross configuration, as in the Figure, or as the wearer grows, the straps can be deployed straight downward from the shoulder, thereby providing a greater effective length, accomodating a longer torso. The width of the strapping is relatively unimportant, and will of course depend upon the size of the garment and individual in general. It has has been found, however, that wider strapping has less tendency to "bunch", and to be more comfortable.

The strapping may be made from any soft, absorbent fabric such as cotton, polyester, cotton/polyester blends, or similar materials.

Figure 4:
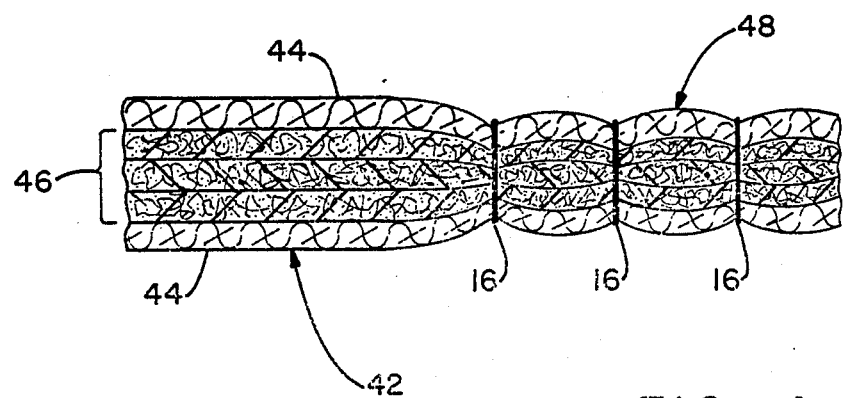
FIG. 4 is a cross section of the garment of the invention along line 4—4 of FIG. 1.

FIG. 4 illustrates a cross-section of the garment of the invention along line 4—4 of FIG. 1. Shown in the Figure is the laminate structure, generally 42, which includes multiple inner layers 46 enclosed in outer layers 44. The attenuated yoke panel portion, generally 48, is included, showing the compressed quilt-like structure achieved by the stitching 16.

The inner layers 46 serve the important function of absorbing and retaining liquid reaching them through outer layers 44. While the inner layers 46 may comprise a single layer of the desired thickness, and hence absorbency, it has been found that multiple layers confer certain benefits, and at least two such layers, preferably three, are preferred. It is for example believed that multiple layers may be capable of holding more moisture than an equal thickness of a single layer, and a multiple layer construction helps to provide greater thermal insulating qualities.

A variety of materials can be used for inner layers 46, such as for instance, cotton, polyester, blends of such materials, and a variety of other cellulosic or different water absorbency materials. The absorbant material may either be of a woven or non-woven variety; however, non-woven material, as for example batting, has a remarkable ability to hold liquid and is preferred. Among suitable materials may be mentioned that sold under the trademark "Thermolam", termed a multi-purpose fleece, by its manufacturer, Stacy Industries of Woodridge, New Jersey.

The outer layers 44 can likewise be fabricated from a wide variety of materials: polyester, cotton, and blends of those materials, being but a few; however, the use of terry cloth, a woven fabric which includes uncut loops forming a pile structure, and which is extremely absorbant is preferred. the use of cotton/polyester blends has the advantage of being soft, and absorbent, characteristics of importance to the comfort of the patient, as well as to the utility of the garment for its intended purpose.

While it will frequently be desirable to construct the garment of the invention from materials and fabrics which are able to withstand repeated washes, it is within the scope of the invention to manufacture them from less durable, inexpensive materials including, but not limited to paper-type products so that they can be disposed of after a single use.

While in accordance with the patent statutes, a preferred embodiment and best mode has been presented, the scope of the invention is not limited thereto, but rather is measured by the scope of the attached claims.

What is claimed is:

1. A medical absorption garment comprising:
   a bib member having upper and lower ends; a torso strap, and upper strapping, wherein said bib member is a laminate comprising at least one absorbent, fibrous inner layer disposed between two outer layers of fabric, said bib member being provided on its upper end with a neck yoke cut from the upper end of said bib member and extending downwardly therefrom, said neck yoke having an attenuated yoke panel adjacent the lower edge of said neck yoke, and said yoke panel comprising at least one absorbent fibrous inner layer disposed between two outer layers of fabric, and means for compressing the thickness of at least a portion of said yoke panel, and
   wherein said torso strap extends from one side of said bib, being adapted to encircle the torso of a wearer, and to be temporarily attached to the other side of said bib member,
   wherein further, said upper strapping extends from the upper end of said bib member, one from each side of said neck yoke, being adapted to be temporarily attached to said torso strap at the rear of the wearer by a strap fastening means.

2. A medical absorption garment according to claim 1 wherein said inner layer comprises batting material, and said yoke panel comprises a portion of the bib which has been attenuated by multiple stitching.

3. A medical absorption garment according to claim 2 wherein said inner layer comprises multiple sheets of polyester batting, and said fabric comprises terry cloth, said sheets being prevented from shifting relative to said outer layers of fabric, and to each other, by means of tack stitching disposed across the face of the bib.

4. A medical absorption garment according to claim 2 wherein said strap fastening means comprises cooperating strips of filamentary hooks and loops, respectively disposed on strips attached to the surface to be temporarily fastened to each other.

5. A medical absorption garment comprising:
   a bib member having upper and lower ends;
   a torso strap;
   two shoulder straps and strap fastening means, wherein said bib member is a laminate comprising multiple sheets of absorbent batting disposed between two outer layers of fabric, said bib member being provided on its upper end with a neck yoke cut from the upper end of said bib member and extending downwardly therefrom, said neck yoke having a panel adjacent to the lower edge of said panel attenuated by stitching, and
   wherein said torso strap extends from one side of said bib, being adapted to encircle the torso of the wearer and to be temporarily attached to said bib member by strap fastening means, and
   wherein further, said shoulder straps extend from the upper end of said bib member, one from each side of said neck yoke, being adapted to be temporarily attached to said torso strap at the rear of the wearer by strap fastening means following extension over the shoulders of the wearer, and
   wherein still further, said strap fastening means comprise cooperating strips of filamentary hooks and loops, respectively disposed as strips attached to the surfaces to be temporarily fastened to each other.

* * * * *